(12) United States Patent
Ochiai

(10) Patent No.: US 8,980,591 B2
(45) Date of Patent: Mar. 17, 2015

(54) PROTEIN HAVING ACTIVITY TO PROMOTE FATTY ACID CHAIN ELONGATION, GENE ENCODING SAME AND USE THEREOF

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 14/235,144

(22) PCT Filed: Aug. 3, 2012

(86) PCT No.: PCT/JP2012/069792
§ 371 (c)(1),
(2), (4) Date: Jan. 27, 2014

(87) PCT Pub. No.: WO2013/018879
PCT Pub. Date: Feb. 7, 2013

(65) Prior Publication Data
US 2014/0242648 A1    Aug. 28, 2014

(30) Foreign Application Priority Data

Aug. 4, 2011 (JP) .................................. 2011-171044

(51) Int. Cl.
| | | |
|---|---|---|
| C12P 7/64 | (2006.01) |
| C12N 9/00 | (2006.01) |
| C12N 1/20 | (2006.01) |
| C12N 15/00 | (2006.01) |
| C07H 21/04 | (2006.01) |
| C12N 9/04 | (2006.01) |
| A61K 31/7088 | (2006.01) |
| A23L 1/30 | (2006.01) |
| C12N 9/10 | (2006.01) |
| C12N 15/80 | (2006.01) |
| A61K 31/00 | (2006.01) |

(52) U.S. Cl.
CPC .......... *C12N 9/0006* (2013.01); *A61K 31/7088* (2013.01); *A23L 1/3006* (2013.01); *C12N 9/1029* (2013.01); *C12N 15/80* (2013.01); *C12P 7/6463* (2013.01); *A61K 31/00* (2013.01)
USPC ..... 435/134; 435/183; 435/252.3; 435/320.1; 536/23.2

(58) Field of Classification Search
None
See application file for complete search history.

(56) References Cited

U.S. PATENT DOCUMENTS

| | | |
|---|---|---|
| 2008/0020124 A1 | 1/2008 | Kawashima et al. |
| 2008/0138874 A1 | 6/2008 | Ochiai et al. |
| 2010/0317622 A1 | 12/2010 | Kawashima et al. |
| 2012/0277451 A1 | 11/2012 | Ochiai |

FOREIGN PATENT DOCUMENTS

| | | |
|---|---|---|
| CN | 1954079 | 4/2007 |
| JP | 2005-287403 | 10/2005 |
| WO | 2010/147138 | 12/2010 |
| WO | 2011/078134 | 6/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kobayashi, "Biseibutsu wa Kisho Yushi no Hoko!?" Biotechnology, Jan. 25, 2010, vol. 88, No. 1, p. 22; along with an English translation.
Parker-Barnes et al., "Identification and Characterization of an Enzyme Involved in the Elongation of n-6 and n-3 Polyunsaturated Fatty Acids," Proc. Natl. Acad. Sci. U.S.A, Jul. 18, 2000, vol. 97, No. 15, pp. 8284-8289.
Takeno et al., "Arachidonic Acid Seisansei Shijokin Mortierella alpina 1S-4 ni Okeru Shibosan Sacho Enchoka Koso (GLELO) Idenshi Hatsugen ni yoru Shibosan Sosei no Kaihen," 2004 Nendo (Heisei 16 Nendo) Japan Society for Bioscience, Biotechnology, and Agrochemistry Taikai Koen Yoshishu, Mar. 5, 2004, p. 25, 2A07a10.
Sakuradani et al., "Arachidonic Acid Seisansei Shijokin Mortierella alpina 1S-4 no Shibosan Sacho Encho Koso Idenshi no Kozo to Kino no Kaimei," 2010 Nendo (Heisei 22 Nendo) Japan Society for Bioscience, Biotechnology, and Agrochemistry Taikai Koen Yoshishu, Mar. 5, 2010, p. 95, 2AUp13.
Kihara et al., "Membrane Topology and Essential Amino Acid Residues of Phs1, a 3-Hydroxyacyl-CoA Dehydratase Involved in Very Long-chain Fatty Acid Elongation," (2008) J. Biol. Chem., vol. 283, No. 17, pp. 11199-11209.
Han et al., "The *Saccharomyces cerevisiae YBR159w* Gene Encodes the 3-Ketoreductase of the Microsomal Fatty Acid Elongase," (2002) J. Biol. Chem., vol. 277, No. 38, pp. 35440-35449.
Athenstaedt et al., "1-Acyldihydroxyacetone-phosphate Reductase (Ayr1p) of the Yeast *Saccharomyces cerevisiae* Encoded by the Open Reading Frame YIL124w Is a Major Component of Lipid Particles," (2000) J. Biol. Chem., vol. 275, No. 1, pp. 235-240.
International Preliminary Report on Patentability for PCT/JP2012/069792, issued Feb. 4, 2014 (including the Written Opinion of the ISA), along with an English translation.
International Search Report for PCT/JP2012/069792, mailed Nov. 6, 2012, along with an English translation.
Japanese Office Action issued with respect to Japanese Patent App. 2013-526962, mailed Apr. 15, 2014.
Office Action issued with respect to Russian Patent Application No. 2014107735, mailed Sep. 22, 2014, along with an English language translation.
Marry et al., "Human Biochemistry", M.: "Mir", 1993, p. 34.

\* cited by examiner

*Primary Examiner* — Christian Fronda
(74) *Attorney, Agent, or Firm* — Greenblum & Bernstein, P.L.C.

(57) ABSTRACT

The present invention relates to a protein having an activity to promote fatty acid chain elongation, a polynucleotide encoding the same, etc. The present invention provides, for example, a polynucleotide containing the nucleotide sequence shown in SEQ ID NO: 1 or 4, a polynucleotide encoding a protein which consists of the amino acid sequence shown in SEQ ID NO: 2, an expression vector and a transformant, each containing such a polynucleotide, a method for preparing lipids or fatty acids by using such a transformant, or a food or the like containing lipids or fatty acids prepared by such a method.

12 Claims, 3 Drawing Sheets

Figure 1

```
            1                                                                                              100
genome   ATGGCCTCGTCTAAAAAGATCGTCCTCGTCACCGGCTGTACCACTGGAGGCATTGGTTATGAAACCGCAAAGGCATTCGAAAAGGTACGCCCTCGGCAGT
cDNA     ATGGCCTCGTCTAAAAAGATCGTCCTCGTCACCGGCTGTACCACTGGAGGCATTGGTTATGAAACCGCAAAGGCATTCGAAAAG 101                                                                                            200
genome   CTCACTTCATGGAAGGCCCCTCTGAGAATTACCAATCAACCAATTTGCAGTTACAGCTGGATTCATTGACTAATCGTGCATACCTTTCTTATACTAAATG
cDNA     ----------------------------------------------------------------------------------------------------

201                                                                                            300
genome   CCTATTCAGAGTGGCTGCAAAGTGTATGCCGCAGCAAGACGTCTCGAAGCCATAACGGGCATTGAAGGTGAGGGTTGTATTTTGCCACAAGTCTTCGTGG
cDNA     ---------AGTGGCTGCAAAGTGTATGCCGCAGCAAGACGTCTCGAAGCCATAACGGGCATTGAAGGT-----------------------------

301                                                                                            400
genome   GTCGTGTGCGGGATGCAGGCATTAACACTCCTTAAATTGCGTGCAGGTCTAGATATCGAAAAGGTCTACATCGACGTACTGGACGAGAAGTCCATCAAAG
cDNA     ----------------------------------------------CTAGATATCGAAAAGGTCTACATCGACGTACTGGACGAGAAGTCCATCAAAG 401                                                                                            500
genome   ACGGCCGTCAACGTAAGATGCCTGCTGTCAACTGTCCTACTTCTACTTGCATAAGTTTTCAATTCTGATCTCTCAGGTCCTTAAACTTGCATTGTAGCACG
cDNA     ACGGCCGTCAAC----------------------------------------------------------------------------------------

501                                                                                            600
genome   TTATCGAGAAGGAAGGACGAATCGGTAAGAGAAGAAACGCGTGTTTTCAGTTCAACGGACGATTGCTCAACATGCAAGAAGACCAAGCATTGATGGCTGC
cDNA     ----------------------------------------------------------------------------------------------------

601                                                                                            700
genome   CTTATATTCTTCATACAGATATTCTGTTCAACAATGCCGGAATGGGACTCGCATGCCCACTGATCGACATGTCTGTAAGTAACACAGGGTGGACATATGA
cDNA     ----------------------------------------------------------------------------------------------------

701                                                                                            800
genome   ACACTGAAAGGCAAACCCCACCTTAGCAGACGGCAAGCACTAACACTTCAGCCTTCATTTAATATGTATAGATTGAGACAACCCGCAAGCTGCTCGACAC
cDNA     ----------------------------------------------------------------ATTGAGACAACCCGCAAGCTGCTCGACAC 801                                                                                            900
genome   CAACATCACCTCCGTCATTCTCGTGTCGAAAGAGGTGGCGCCTCATATGATTAGACAAAAGTCTGGTCTGATTGTCAATGTTGGCTCAGTCACAGCCTAT
cDNA     CAACATCACCTCCGTCATTCTCGTGTCGAAAGAGGTGGCGCCTCATATGATTAGACAAAAGTCTGGTCTGATTGTCAATGTTGGCTCAGTCACAGCCTAT 901                                                                                            1000
genome   CTCGCGACACCTTGGGGCGGTCTCTATGCTGCCAGCAAGGCCGCAGTGCACTCCATCTCGGACGCACTGCGCATGGAGTTGGCTCCCTTTGGTGTTGATG
cDNA     CTCGCGACACCTTGGGGCGGTCTCTATGCTGCCAGCAAGGCCGCAGTGCACTCCATCTCGGACGCACTGCGCATGGAGTTGGCTCCCTTTGGTGTTGATG 1001                                                                                           1100
genome   TTTCGGTCGTGGCGGCCTGGTGCAATCAAGTCCAACATCGGTGACAACAACTTGAAGGCCTTCCATCTTCCCGAGAGTAAGTTCAACCAGCAATTCCGTCC
cDNA     TTTCGGTCGTGGCGGCCTGGTGCAATCAAGTCCAACATCGGTGACAACAACTTGAAGGCCTTCCATCTTCCCGAGA 1101                                                                                           1200
genome   GCTTGAAGCTGCAATCATATTCCCTTCAGCCAAATTCCTCATATGCTCATACTGCCTTGTTATTTTTTTTTTTTCCTTCTTTGTTGAAATCTCAAGATTC
cDNA     ----------------------------------------------------------------------------------------------------

1201                                                                                           1300
genome   CTTCTATCAGTCTGTCATCAGCTATATCATGTCCAGAGCAAATGCTTCCCAAGGTAAGACGCGTCGATTTCACTGACGATCTGCCAACAATGGAAAAAAA
cDNA     ----------------------------------------------------------------------------------------------------

1301                                                                                           1400
genome   ACCGTTGCGTCTTGATGCTACTGACTTGTGTCTCTGACACTCACTGTGCCCCCATCTTGTTTATCCATCAGCCCCTGGATGCACACCCACTGCCAAGTTT
cDNA     ------------------------------------------------------------------------CCCCTGGATGCACACCCACTGCCAAGTTT 1401                                                                                           1500
genome   GCAAAGTACGTCGTGGCAAAGTGCCTCAAGTCATCCCCCCCTCGATACATCGATTACGGCACGCTGTCAAACCTCTTCCGATTCTTGCGCTACGCGCCCT
cDNA     GCAAAGTACGTCGTGGCAAAGTGCCTCAAGTCATCCCCCCCTCGATACATCGATTACGGCACGCTGTCAAACCTCTTCCGATTCTTGCGCTACGCGCCCT 1501                                                         1589
genome   GGATGATCACGGACTTCATCTTCTCCCGCAAATTTGGTCTGAATGTTCTCCAGAAGTCGGTAAAGGATGGCAAGGTCGTTGGAAAGTAG
cDNA     GGATGATCACGGACTTCATCTTCTCCCGCAAATTTGGTCTGAATGTTCTCCAGAAGTCGGTAAAGGATGGCAAGGTCGTTGGAAAGTAG
```

Figure 2

```
  1  ATGGCCTCGT CTAAAAAGAT CGTCCTCGTC ACCGGCTGTA CCACTGGAGG CATTGGTTAT
      M  A  S  S  K  K  I  V  L  V  T  G  C  T  T  G  G  I  G  Y

61  GAAACCGCAA AGGCATTCGA AAAGAGTGGC TGCAAAGTGT ATGCCGCAGC AAGACGTCTC
      E  T  A  K  A  F  E  K  S  G  C  K  V  Y  A  A  A  R  R  L

121  GAAGCCATAA CGGGCATTGA AGGTCTAGAT ATCGAAAAGG TCTACATCGA CGTACTGGAC
      E  A  I  T  G  I  E  G  L  D  I  E  K  V  Y  I  D  V  L  D

181  GAGAAGTCCA TCAAAGACGC CGTCAACATT GAGACAACCC GCAAGCTGCT CGACACCAAC
      E  K  S  I  K  D  A  V  N  I  E  T  T  R  K  L  L  D  T  N

241  ATCACCTCCG TCATTCTCGT GTCCAAAGAG GTGGCGCCTC ATATGATTAG ACAAAAGTCT
      I  T  S  V  I  L  V  S  K  E  V  A  P  H  M  I  R  Q  K  S

301  GGTCTGATTG TCAATGTTGG CTCAGTCACA GCCTATCTCG CGACACCTTG GGGCGGTCTC
      G  L  I  V  N  V  G  S  V  T  A  Y  L  A  T  P  W  G  G  L

361  TATGCTGCCA GCAAGGCCGC AGTGCACTCC ATCTCGGACG CACTGCGCAT GGAGTTGGCT
      Y  A  A  S  K  A  A  V  H  S  I  S  D  A  L  R  M  E  L  A

421  CCCTTTGGTG TTGATGTTTC GGTCGTGGCG CCTGGTGCAA TCAAGTCCAA CATCGGTGAC
      P  F  G  V  D  V  S  V  V  A  P  G  A  I  K  S  N  I  G  D

481  AACAACTTGA AGGCCTTCCA TCTTCCCGAG ACCCCTGGAT GCACACCCAC TGCCAAGTTT
      N  N  L  K  A  F  H  L  P  E  T  P  G  C  T  P  T  A  K  F

541  GCAAAGTACG TCGTGGCAAA GTGCCTCAAG TCATCCCCCC CTCGATACAT CGATTACGGC
      A  K  Y  V  V  A  K  C  L  K  S  S  P  P  R  Y  I  D  Y  G

601  ACGCTGTCAA ACCTCTTCCG ATTCTTGCGC TACGCGCCCT GGATGATCAC GGACTTCATC
      T  L  S  N  L  F  R  F  L  R  Y  A  P  W  M  I  T  D  F  I

661  TTCTCCCGCA AATTTGGTCT GAATGTTCTC CAGAAGTCGG TAAAGGATGG CAAGGTCGTT
      F  S  R  K  F  G  L  N  V  L  Q  K  S  V  K  D  G  K  V  V

721  GGAAAGTAG
      G  K  *
```

Figure 3

```
                    1                                                50
        MaADR1      ---MASSKKIVLVTGCTTGGIGYETAKAFEKSGCKVYAAARRLEAITGIE
   XP_002946364     MAVRPSRGNVVLITGCSDGGIGAALSKAFHEAGCTVFATARRLEAMASLR
        ScAYR1      MSELQSQPKKIAVVTGASGGIGYEVTKELARNGYLVYACARRLEPMAQLA 51                                               100
        MaADR1      GLD----IEKVYIDVLDEKSIKDAVN------------------------
   XP_002946364     ELG----IRTVALDVTNDDSVKTAVSAVLA--EAGRIDILVNNAGMGLVA
        ScAYR1      IQFGNDSIKPYKLDISKPEEIVTFSGFLRANLPDGKLDLLYNNAGQSCTF 101                                              150
        MaADR1      -------IETTRKLLDTNITSVILVSKEVAPHMIRQKSGLIVNVGSVTAYL
   XP_002946364     PVAEVDIQEAQEVFDTNYWGTLRMVQAVSPHMATRRSGLICNVGSVVGFI
        ScAYR1      PALDATDAAVEQCFKVNVFGHINMCRELSEFLIKAK-GTIVFTGSLAGVV 151                                              200
        MaADR1      ATPWGGLYAASKAAVHSISDALRMELAPFGVDVSVVAPGAIKSNIGDNNL
   XP_002946364     STPWGAIYSSSKAAVHSLTDALRLEMRPFGVRVVLLAPGAVKSNIGTNNL
        ScAYR1      SFPFGSIYSASKAAIHQYARGLHLEMKPFNVRVINAITGGVATDIADKRP
                                     *
                    201                                              250
        MaADR1      KAFH-------------------LPETPGCTPTAKFAKYVVAKCLKSSPPR
   XP_002946364     KRFGGQFTLYAPFVDVIRERTVMSQGTESMPTDTFARRVVRELLRPCPPR
        ScAYR1      LPETSIYNFPEGR-EAFNSRKTMAKDNKPMPADAYAKQLVKDILSTSDPV 251                                              300
        MaADR1      YIDYGTLSNLFRFLR-YAPWMITDFIFSRKFGLNVLQKSVKDGKVVGK--
   XP_002946364     RFLLGGFVPLMKVVM-WWPLWLKDWLLKRTFKMNTVRLPASPVAPVAAGA
        ScAYR1      DVYRGTFANIMRFVMIFVPYWLLEKGLSKKFKLDKVNNALKSKQKNKDD-

301
        MaADR1      ----
   XP_002946364     KKLD
        ScAYR1      ----
```

Double underlined part represents NADPH binding site
Asterisk (*) represents active centre

SEQUENCE LISTING

```
<160> NUMBER OF SEQ ID NOS: 8

<210> SEQ ID NO 1
<211> LENGTH: 726
<212> TYPE: DNA
<213> ORGANISM: Mortierella alpina

<400> SEQUENCE: 1
atggcctcgt ctaaaaagat cgtcctcgtc accggctgta ccactggagg cattggttat      60
gaaaccgcaa aggcattcga aaagagtggc tgcaaagtgt atgccgcagc aagacgtctc     120
```

```
gaagccataa cgggcattga aggtctagat atcgaaaagg tctacatcga cgtactggac    180
gagaagtcca tcaaagacgc cgtcaacatt gagacaaccc gcaagctgct cgacaccaac    240
atcacctccg tcattctcgt gtccaaagag gtggcgcctc atatgattag acaaaagtct    300
ggtctgattg tcaatgttgg ctcagtcaca gcctatctcg cgacacctttg ggcggtctc    360 tatgctgcca gcaaggccgc agtgcactcc atctcggacg cactgcgcat ggagttggct    420
ccctttggtg ttgatgtttc ggtcgtggcg cctggtgcaa tcaagtccaa catcggtgac    480
aacaacttga aggccttcca tcttcccgag acccctggat gcacacccac tgccaagttt    540
gcaaagtacg tcgtggcaaa gtgcctcaag tcatccccc ctcgatacat cgattacggc    600
acgctgtcaa acctcttccg attcttgcgc tacgcgccct ggatgatcac ggacttcatc    660
ttctcccgca aatttggtct gaatgttctc cagaagtcgg taaaggatgg caaggtcgtt    720
ggaaag                                                               726
```

```
<210> SEQ ID NO 2
<211> LENGTH: 242
<212> TYPE: PRT
<213> ORGANISM: Mortierella alpina

<400> SEQUENCE: 2

Met Ala Ser Ser Lys Lys Ile Val Leu Val Thr Gly Cys Thr Thr Gly
1               5                   10                  15

Gly Ile Gly Tyr Glu Thr Ala Lys Ala Phe Glu Lys Ser Gly Cys Lys
            20                  25                  30

Val Tyr Ala Ala Ala Arg Arg Leu Glu Ala Ile Thr Gly Ile Glu Gly
        35                  40                  45

Leu Asp Ile Glu Lys Val Tyr Ile Asp Val Leu Asp Glu Lys Ser Ile
    50                  55                  60

Lys Asp Ala Val Asn Ile Glu Thr Thr Arg Lys Leu Leu Asp Thr Asn
65                  70                  75                  80

Ile Thr Ser Val Ile Leu Val Ser Lys Glu Val Ala Pro His Met Ile
                85                  90                  95

Arg Gln Lys Ser Gly Leu Ile Val Asn Val Gly Ser Val Thr Ala Tyr
            100                 105                 110

Leu Ala Thr Pro Trp Gly Gly Leu Tyr Ala Ala Ser Lys Ala Ala Val
        115                 120                 125

His Ser Ile Ser Asp Ala Leu Arg Met Glu Leu Ala Pro Phe Gly Val
    130                 135                 140

Asp Val Ser Val Val Ala Pro Gly Ala Ile Lys Ser Asn Ile Gly Asp
145                 150                 155                 160

Asn Asn Leu Lys Ala Phe His Leu Pro Glu Thr Pro Gly Cys Thr Pro
                165                 170                 175

Thr Ala Lys Phe Ala Lys Tyr Val Val Ala Lys Cys Leu Lys Ser Ser
            180                 185                 190

Pro Pro Arg Tyr Ile Asp Tyr Gly Thr Leu Ser Asn Leu Phe Arg Phe
        195                 200                 205

Leu Arg Tyr Ala Pro Trp Met Ile Thr Asp Phe Ile Phe Ser Arg Lys
    210                 215                 220

Phe Gly Leu Asn Val Leu Gln Lys Ser Val Lys Asp Gly Lys Val Val
225                 230                 235                 240

Gly Lys

<210> SEQ ID NO 3
```

```
<211> LENGTH: 729
<212> TYPE: DNA
<213> ORGANISM: Mortierella alpina
<220> FEATURE:
<221> NAME/KEY: CDS
<222> LOCATION: (1)..(726)

<400> SEQUENCE: 3 atg gcc tcg tct aaa aag atc gtc ctc gtc acc ggc tgt acc act gga      48
Met Ala Ser Ser Lys Lys Ile Val Leu Val Thr Gly Cys Thr Thr Gly
1               5                  10                  15 ggc att ggt tat gaa acc gca aag gca ttc gaa aag agt ggc tgc aaa      96
Gly Ile Gly Tyr Glu Thr Ala Lys Ala Phe Glu Lys Ser Gly Cys Lys
            20                  25                  30 gtg tat gcc gca gca aga cgt ctc gaa gcc ata acg ggc att gaa ggt     144
Val Tyr Ala Ala Ala Arg Arg Leu Glu Ala Ile Thr Gly Ile Glu Gly
        35                  40                  45 cta gat atc gaa aag gtc tac atc gac gta ctg gac gag aag tcc atc     192
Leu Asp Ile Glu Lys Val Tyr Ile Asp Val Leu Asp Glu Lys Ser Ile
    50                  55                  60 aaa gac gcc gtc aac att gag aca acc cgc aag ctg ctc gac acc aac     240
Lys Asp Ala Val Asn Ile Glu Thr Thr Arg Lys Leu Leu Asp Thr Asn
65                  70                  75                  80 atc acc tcc gtc att ctc gtg tcc aaa gag gtg gcg cct cat atg att     288
Ile Thr Ser Val Ile Leu Val Ser Lys Glu Val Ala Pro His Met Ile
                85                  90                  95 aga caa aag tct ggt ctg att gtc aat gtt ggc tca gtc aca gcc tat     336
Arg Gln Lys Ser Gly Leu Ile Val Asn Val Gly Ser Val Thr Ala Tyr
            100                 105                 110 ctc gcg aca cct tgg ggc ggt ctc tat gct gcc agc aag gcc gca gtg     384
Leu Ala Thr Pro Trp Gly Gly Leu Tyr Ala Ala Ser Lys Ala Ala Val
        115                 120                 125 cac tcc atc tcg gac gca ctg cgc atg gag ttg gct ccc ttt ggt gtt     432
His Ser Ile Ser Asp Ala Leu Arg Met Glu Leu Ala Pro Phe Gly Val
    130                 135                 140 gat gtt tcg gtc gtg gcg cct ggt gca atc aag tcc aac atc ggt gac     480
Asp Val Ser Val Val Ala Pro Gly Ala Ile Lys Ser Asn Ile Gly Asp
145                 150                 155                 160 aac aac ttg aag gcc ttc cat ctt ccc gag acc cct gga tgc aca ccc     528
Asn Asn Leu Lys Ala Phe His Leu Pro Glu Thr Pro Gly Cys Thr Pro
                165                 170                 175 act gcc aag ttt gca aag tac gtc gtg gca aag tgc ctc aag tca tcc     576
Thr Ala Lys Phe Ala Lys Tyr Val Val Ala Lys Cys Leu Lys Ser Ser
            180                 185                 190 ccc cct cga tac atc gat tac ggc acg ctg tca aac ctc ttc cga ttc     624
Pro Pro Arg Tyr Ile Asp Tyr Gly Thr Leu Ser Asn Leu Phe Arg Phe
        195                 200                 205 ttg cgc tac gcg ccc tgg atg atc acg gac ttc atc ttc tcc cgc aaa     672
Leu Arg Tyr Ala Pro Trp Met Ile Thr Asp Phe Ile Phe Ser Arg Lys
    210                 215                 220 ttt ggt ctg aat gtt ctc cag aag tcg gta aag gat ggc aag gtc gtt     720
Phe Gly Leu Asn Val Leu Gln Lys Ser Val Lys Asp Gly Lys Val Val
225                 230                 235                 240 gga aag tag                                                          729
Gly Lys <210> SEQ ID NO 4
<211> LENGTH: 1589
<212> TYPE: DNA
<213> ORGANISM: Mortierella alpina

<400> SEQUENCE: 4
```

-continued

| | |
|---|---|
| atggcctcgt ctaaaaagat cgtcctcgtc accggctgta ccactggagg cattggttat | 60 |
| gaaaccgcaa aggcattcga aaaggtacgc cctcggcagt ctcacttcat ggaaggcccc | 120 |
| tctgagaatt accaatcaac caatttgcag ttacagctgg attcattgac taatcgtgca | 180 |
| taccttctt atactaaatg cctattcaga gtggctgcaa agtgtatgcc gcagcaagac | 240 |
| gtctcgaagc cataacgggc attgaaggtg agggttgtat tttgccacaa gtcttcgtgg | 300 |
| gtcgtgtgcg ggatgcaggc attaacactc cttaaattgc gtgcaggtct agatatcgaa | 360 |
| aaggtctaca tcgacgtact ggacgagaag tccatcaaag acgccgtcaa cgtaagatgc | 420 |
| ctgctgtcaa ctgtcctact tctacttgca taagttttca attctgatct ctcaggtcct | 480 |
| taaacttgca ttgtagcacg ttatcgagaa ggaaggacga atcggtaaga aagaaacgc | 540 |
| gtgttttcag ttcaacggac gattgctcaa catgcaagaa gaccaagcat tgatggctgc | 600 |
| cttatattct tcatacagat attctgttca acaatgccgg aatgggactc gcatgcccac | 660 |
| tgatcgacat gtctgtaagt aacacagggt ggacatatga acactgaaag gcaaaccccca | 720 |
| ccttagcaga cggcaagcac taacacttca gccttcattt aatatgtata gattgagaca | 780 |
| acccgcaagc tgctcgacac caacatcacc tccgtcattc tcgtgtccaa agaggtggcg | 840 |
| cctcatatga ttagacaaaa gtctggtctg attgtcaatg ttggctcagt cacagcctat | 900 |
| ctcgcgacac cttggggcgg tctctatgct gccagcaagg ccgcagtgca ctccatctcg | 960 |
| gacgcactgc gcatggagtt ggctcccttt ggtgttgatg tttcggtcgt ggcgcctggt | 1020 |
| gcaatcaagt ccaacatcgg tgacaacaac ttgaaggcct tccatcttcc cgagagtaag | 1080 |
| ttcaaccagc aattccgtcc gcttgaagct gcaatcatat tcccttcagc caaattcctc | 1140 |
| atatgctcat actgccttgt tatttttttt ttttccttct ttgttgaaat ctcaagattc | 1200 |
| cttctatcag tctgtcatca gctatatcat gtccagagca aatgcttccc aaggtaagac | 1260 |
| gcgtcgattt cactgacgat ctgccaacaa tggaaaaaaa accgttgcgt cttgatgcta | 1320 |
| ctgacttgtg tctctgacac tcactgtgcc cccatcttgt ttatccatca gcccctggat | 1380 |
| gcacacccac tgccaagttt gcaaagtacg tcgtggcaaa gtgcctcaag tcatccccccc | 1440 |
| ctcgatacat cgattacggc acgctgtcaa acctcttccg attcttgcgc tacgcgccct | 1500 |
| ggatgatcac ggacttcatc ttctcccgca aatttggtct gaatgttctc cagaagtcgg | 1560 |
| taaaggatgg caaggtcgtt ggaaagtag | 1589 |

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggatccatgg cctcgtctaa aaagatcgtc ct                                    32

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcgactact ttccaacgac cttgccatcc                                      30

<210> SEQ ID NO 7
<211> LENGTH: 297
<212> TYPE: PRT
<213> ORGANISM: Volvox carteri

<400> SEQUENCE: 7

```
Met Ala Val Arg Pro Ser Arg Gly Asn Val Val Leu Ile Thr Gly Cys
1               5                   10                  15

Ser Asp Gly Gly Ile Gly Ala Ala Leu Ser Lys Ala Phe His Glu Ala
            20                  25                  30

Gly Cys Thr Val Phe Ala Thr Ala Arg Arg Leu Glu Ala Met Ala Ser
        35                  40                  45

Leu Arg Glu Leu Gly Ile Arg Thr Val Ala Leu Asp Val Thr Asn Asp
    50                  55                  60

Asp Ser Val Lys Thr Ala Val Ser Ala Val Leu Ala Glu Ala Gly Arg
65                  70                  75                  80

Ile Asp Ile Leu Val Asn Asn Ala Gly Met Gly Leu Val Ala Pro Val
                85                  90                  95

Ala Glu Val Asp Ile Gln Glu Ala Gln Glu Val Phe Asp Thr Asn Tyr
            100                 105                 110

Trp Gly Thr Leu Arg Met Val Gln Ala Val Ser Pro His Met Ala Thr
        115                 120                 125

Arg Arg Ser Gly Leu Ile Cys Asn Val Gly Ser Val Val Gly Phe Ile
    130                 135                 140

Ser Thr Pro Trp Gly Ala Ile Tyr Ser Ser Ser Lys Ala Ala Val His
145                 150                 155                 160

Ser Leu Thr Asp Ala Leu Arg Leu Glu Met Arg Pro Phe Gly Val Arg
                165                 170                 175

Val Val Leu Leu Ala Pro Gly Ala Val Lys Ser Asn Ile Gly Thr Asn
            180                 185                 190

Asn Leu Lys Arg Phe Gly Gly Gln Phe Thr Leu Tyr Ala Pro Phe Val
        195                 200                 205

Asp Val Ile Arg Glu Arg Thr Val Met Ser Gln Gly Thr Glu Ser Met
    210                 215                 220

Pro Thr Asp Thr Phe Ala Arg Arg Val Val Arg Glu Leu Leu Arg Pro
225                 230                 235                 240

Cys Pro Pro Arg Arg Phe Leu Leu Gly Gly Phe Val Pro Leu Met Lys
                245                 250                 255

Val Val Met Trp Trp Pro Leu Trp Leu Lys Asp Trp Leu Leu Lys Arg
            260                 265                 270

Thr Phe Lys Met Asn Thr Val Arg Leu Pro Ala Ser Pro Val Ala Pro
        275                 280                 285

Val Ala Ala Gly Ala Lys Lys Leu Asp
    290                 295
```

<210> SEQ ID NO 8
<211> LENGTH: 297
<212> TYPE: PRT
<213> ORGANISM: Saccharomyces cerevisiae

<400> SEQUENCE: 8

```
Met Ser Glu Leu Gln Ser Gln Pro Lys Lys Ile Ala Val Val Thr Gly
1               5                   10                  15

Ala Ser Gly Gly Ile Gly Tyr Glu Val Thr Lys Glu Leu Ala Arg Asn
```

-continued

```
                20                  25                  30
Gly Tyr Leu Val Tyr Ala Cys Ala Arg Arg Leu Glu Pro Met Ala Gln
            35                  40                  45

Leu Ala Ile Gln Phe Gly Asn Asp Ser Ile Lys Pro Tyr Lys Leu Asp
 50                  55                  60

Ile Ser Lys Pro Glu Glu Ile Val Thr Phe Ser Gly Phe Leu Arg Ala
 65                  70                  75                  80

Asn Leu Pro Asp Gly Lys Leu Asp Leu Leu Tyr Asn Asn Ala Gly Gln
             85                  90                  95

Ser Cys Thr Phe Pro Ala Leu Asp Ala Thr Asp Ala Ala Val Glu Gln
            100                 105                 110

Cys Phe Lys Val Asn Val Phe Gly His Ile Asn Met Cys Arg Glu Leu
            115                 120                 125

Ser Glu Phe Leu Ile Lys Ala Lys Gly Thr Ile Val Phe Thr Gly Ser
            130                 135                 140

Leu Ala Gly Val Val Ser Phe Pro Phe Gly Ser Ile Tyr Ser Ala Ser
145                 150                 155                 160

Lys Ala Ala Ile His Gln Tyr Ala Arg Gly Leu His Leu Glu Met Lys
            165                 170                 175

Pro Phe Asn Val Arg Val Ile Asn Ala Ile Thr Gly Gly Val Ala Thr
            180                 185                 190

Asp Ile Ala Asp Lys Arg Pro Leu Pro Glu Thr Ser Ile Tyr Asn Phe
            195                 200                 205

Pro Glu Gly Arg Glu Ala Phe Asn Ser Arg Lys Thr Met Ala Lys Asp
            210                 215                 220

Asn Lys Pro Met Pro Ala Asp Ala Tyr Ala Lys Gln Leu Val Lys Asp
225                 230                 235                 240

Ile Leu Ser Thr Ser Asp Pro Val Asp Val Tyr Arg Gly Thr Phe Ala
                245                 250                 255

Asn Ile Met Arg Phe Val Met Ile Phe Val Pro Tyr Trp Leu Leu Glu
                260                 265                 270

Lys Gly Leu Ser Lys Lys Phe Lys Leu Asp Lys Val Asn Asn Ala Leu
            275                 280                 285

Lys Ser Lys Gln Lys Asn Lys Asp Asp
            290                 295
```

PROTEIN HAVING ACTIVITY TO PROMOTE FATTY ACID CHAIN ELONGATION, GENE ENCODING SAME AND USE THEREOF

SEQUENCE LISTING

The instant application contains a Sequence Listing which has been submitted electronically in ASCII format and is hereby incorporated by reference in its entirety. Said ASCII copy, created on Apr. 10, 2014, is named P44540_SL.txt and is 15,206bytes in size.

TECHNICAL FIELD

The present invention relates to a novel protein having an activity to promote fatty acid chain elongation, a polynucleotide encoding the same and use thereof.

BACKGROUND ART

In yeast and other microorganisms, the chain elongation reaction of fatty acids occurs through four steps, i.e., (i) condensation reaction between fatty acid acyl-CoA and malonyl-CoA, (ii) reduction reaction of the condensation product 3-oxoacyl-CoA, (iii) dehydration reaction of 3-hydroxyacyl-CoA, and (iv) reduction reaction of trans-2-enoyl-CoA, whereby the number of carbon atoms is increased by two per cycle of these steps to elongate the chain length (Non-patent Document 1).

The reactions in the above steps (i) to (iv) are known to be catalyzed by enzymes (i) 3-ketoacyl-CoA synthase, (ii) β-ketoacyl reductase, (iii) 3-hydroxyacyl-CoA dehydrogenase, and (iv) enoyl-CoA reductase, respectively (Non-patent Document 1).

Among these enzymes, 3-ketoacyl-CoA synthase which is responsible for condensation reaction is known to have specificity with respect to fatty acids serving as substrates, and enzymes having different specificities have been cloned from various organisms.

In particular, in yeast which has been most well studied among fungi, for all the four steps of fatty acid chain elongation reaction, there have been identified an enzyme responsible for the reaction in each step and a gene encoding the same.

For example, there are two genes IFA38 and AYR1 in yeast, each of which is known to encode an enzyme responsible for β-ketoacyl reductase activity, and it is further known that simultaneous deletion of both genes is lethal (Non-patent Document 2). Moreover, the AYR1 gene is also known to have 1-acyl dihydroxyacetone phosphate reductase activity (Non-patent Document 3).

On the other hand, PHS1 (essential) is known as a gene encoding an enzyme responsible for 3-hydroxyacyl-CoA dehydrogenase activity, while TSC13 (essential) is reported as a gene encoding an enzyme responsible for enoyl-CoA reductase activity.

In contrast, a lipid-producing fungus, *Mortierella alpina* (*M. alpina*)), is known to have 3-ketoacyl-CoA synthase (so-called elongase) genes (MALCE1 (ELO3), MALCE2, GLELO, MAELO) responsible for the first reaction involved in fatty acid chain elongation (Patent Document 1), although genes for enzymes other than 3-ketoacyl-CoA synthase have not yet been identified.

PRIOR ART DOCUMENTS

Patent Documents

Patent Document 1: WO2010/147138

Non-Patent Documents

Non-patent Document 1: Kihara A., et al., (2008) J. Biol. Chem. 283, 11199-11209
Non-patent Document 2: Han, G et al., (2002) J. Biol. Chem. 277, 35440-35449
Non-patent Document 3: Athenstaedt, K., and Daum, G. (2000) J. Biol. Chem. 275, 235-240

DISCLOSURE OF THE INVENTION

Under these circumstances, there is a demand for obtaining a new protein involved in fatty acid chain elongation reaction in *M. alpina* cells or a gene encoding this protein.

As a result of extensive and intensive efforts, the inventors of the present invention have succeeded in cloning a gene encoding MaADR1, a homolog protein of AYR1 which is yeast 3-hydroxyacyl-CoA dehydrogenase, and thereby have completed the present invention. Namely, the present invention provides a polynucleotide, a protein, an expression vector, a transformant, a method for preparing a lipid or fatty acid composition and a food or the like by using such a transformant, as well as a food or the like prepared by such a method, as shown below.

In more detail, the present invention is as follows.

[1] A polynucleotide of any one selected from the group consisting of (a) to (e) shown below:
(a) a polynucleotide containing the nucleotide sequence shown in SEQ ID NO: 1 or 4;
(b) a polynucleotide encoding a protein which consists of the amino acid sequence shown in SEQ ID NO: 2;
(c) a polynucleotide encoding a protein which consists of an amino acid sequence with deletion, substitution, insertion and/or addition of 1 to 100 amino acids in the amino acid sequence shown in SEQ ID NO: 2 and which has an activity to promote fatty acid chain elongation;
(d) a polynucleotide encoding a protein which has an amino acid sequence sharing an identity of 60% or more with the amino acid sequence shown in SEQ ID NO: 2 and which has an activity to promote fatty acid chain elongation; and
(e) a polynucleotide which is hybridizable under stringent conditions with a polynucleotide consisting of a nucleotide sequence complementary to the nucleotide sequence shown in SEQ ID NO: 1 or 4 and which encodes a protein having an activity to promote fatty acid chain elongation.
[2] The polynucleotide according to [1] above, which is any one of (f) or (g) shown below:
(f) a polynucleotide encoding a protein which consists of an amino acid sequence with deletion, substitution, insertion and/or addition of 1 to 10 amino acids in the amino acid sequence shown in SEQ ID NO: 2 and which has an activity to promote fatty acid chain elongation; and
(g) a polynucleotide encoding a protein which has an amino acid sequence sharing an identity of 75% or more with the amino acid sequence shown in SEQ ID NO: 2 and which has an activity to promote fatty acid chain elongation.
[3] The polynucleotide according to [1] above, which contains the nucleotide sequence shown in SEQ ID NO: 1 or 4.
[4] The polynucleotide according to [1] above, which encodes a protein consisting of the amino acid sequence shown in SEQ ID NO: 2.

[5] The polynucleotide according to any one of [1] to [4] above, which is DNA.
[6] A protein encoded by the polynucleotide according to any one of [1] to [5] above.
[7] A vector containing the polynucleotide according to any one of [1] to [5] above.
[8] A non-human transformant transformed with the polynucleotide according to any one of [1] to [5] above.
[9] A non-human transformant transformed with the vector according to [7] above.
[10] The transformant according to [8] or [9] above, wherein the transformant is a lipid-producing fungus.
[11] The transformant according to [10] above, wherein the lipid-producing fungus is *Mortierella alpina*.
[12] A method for preparing a lipid or fatty acid composition, which comprises collecting a lipid or fatty acid composition from a cultured product of the transformant according to any one of [8] to [11] above.
[13] The method according to [12] above, wherein the lipid is a triacylglycerol.
[14] The method according to [12] above, wherein the fatty acid has 18 or more carbon atoms.
[15] A food, a pharmaceutical preparation, a cosmetic preparation or a soap, which contains the lipid or fatty acid composition collected by the method according to [12] above.

The polynucleotide of the present invention can be used for transformation of lipid-producing fungi (e.g., *M. alpina*), yeast, plants and so on. The thus obtained transformed lipid-producing fungi, transformed yeast or transformed plants and so on can be used for manufacture of fatty acid compositions, foods, cosmetic preparations, pharmaceutical preparations, soaps, etc.

More specifically, the transformants of the present invention are extremely high in the efficiency of lipid and fatty acid production. Thus, the present invention can be used effectively for manufacture of pharmaceutical preparations or health foods which require lipids or fatty acids in large quantity.

BRIEF DESCRIPTION OF THE DRAWINGS

FIG. 1 shows an alignment of the genomic (SEQ ID NO: 4) and CDS (SEQ ID NO: 3) sequences of MaADR1.
FIG. 2 shows the CDS sequence of MaADR1 (SEQ ID NO: 3), along with its deduced amino acid sequence (SEQ ID NO: 2).
FIG. 3 shows an amino acid sequence alignment of MaADR1 (SEQ ID NO: 2), a putative protein derived from *Volvox carterif. nagariensis*(green algae) (GENEBANK accession No. XP_002946364) (SEQ ID NO: 7) and AYR1p derived from *S. cerevisiae*(SEQ ID NO: 8) (in the figure, the double-underlined segment represents the NADPH binding site, and the asterisk (*) represents the active center).

BEST MODES FOR CARRYING OUT THE INVENTION

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2011-171044 (filed on Aug. 4, 2011), based on which the present application claims priority.

As described in detail later in the Example section, the inventors of the present invention have succeeded, ahead of others, in cloning the full-length cDNA of an AYR1 homolog gene (MaADR1) from a lipid-producing fungus, *M. alpina*. Moreover, the inventors of the present invention have also identified the nucleotide sequence of *M. alpina*-derived MaADR1 genomic DNA and the deduced amino acid sequence thereof. The ORF sequence, deduced amino acid sequence, CDS sequence and genomic sequence of MaADR1 are as shown in SEQ ID NO: 1, SEQ ID NO: 2, SEQ ID NO: 3 and SEQ ID NO: 4, respectively. These polynucleotides and enzymes can be obtained by procedures as described later in the Example section, known genetic engineering procedures, known synthesis procedures, etc.

1. Polynucleotides of the Present Invention

First, the present invention provides a polynucleotide of any one selected from the group consisting of (a) to (e) shown below.

(a) a polynucleotide containing the nucleotide sequence shown in SEQ ID NO: 1 or 4;
(b) a polynucleotide encoding a protein which consists of the amino acid sequence shown in SEQ ID NO: 2;
(c) a polynucleotide encoding a protein which consists of an amino acid sequence with deletion, substitution, insertion and/or addition of 1 to 100 amino acids in the amino acid sequence shown in SEQ ID NO: 2 and which has an activity to promote fatty acid chain elongation;
(d) a polynucleotide encoding a protein which has an amino acid sequence sharing an identity of 60% or more with the amino acid sequence shown in SEQ ID NO: 2 and which has an activity to promote fatty acid chain elongation; and
(e) a polynucleotide which is hybridizable under stringent conditions with a polynucleotide consisting of a nucleotide sequence complementary to the nucleotide sequence shown in SEQ ID NO: 1 or 4 and which encodes a protein having an activity to promote fatty acid chain elongation.

As used herein, the term "polynucleotide" is intended to mean DNA or RNA.

As used herein, the expression "polynucleotide which is hybridizable under stringent conditions" is intended to mean, for example, a polynucleotide that can be obtained by means of colony hybridization, plaque hybridization, Southern hybridization or other hybridization techniques using, as a probe, the whole or a part of a polynucleotide consisting of a nucleotide sequence complementary to the nucleotide sequence shown in SEQ ID NO: 1 or 4 or a polynucleotide consisting of a nucleotide sequence encoding the amino acid sequence shown in SEQ ID NO: 2. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the term "stringent conditions" may be any of low stringent conditions, moderately stringent conditions and high stringent conditions. "Low stringent conditions" refer to, for example, conditions of 5×SSC, 5× Denhardt's solution, 0.5% SDS, 50% formamide and 32° C. Likewise, "moderately stringent conditions" refer to, for example, conditions of 5×SSC, 5× Denhardt's solution, 0.5% SDS, 50% formamide and 42° C. or conditions of 5×SSC, 1% SDS, 50 mM Tris-HCl (pH 7.5), 50% formamide and 42° C. "High stringent conditions" refer to, for example, conditions of 5×SSC, 5×Denhardt's solution, 0.5% SDS, 50% formamide and 50° C. or conditions of 0.2×SSC, 0.1% SDS and 65° C. Under these conditions, it can be expected that DNA having a higher identity is efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the nucleotide sequence shown in SEQ ID NO: 1 or 4 or a nucleotide sequence encoding the amino acid sequence shown in SEQ ID NO: 2, a DIG nucleic acid detection kit (Roche Diagnostics) may be used for detection of hybridization.

In addition to those listed above, other hybridizable polynucleotides include DNA sharing an identity of 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with DNA shown in SEQ ID NO: 1 or 4 or with DNA encoding the amino acid sequence shown in SEQ ID NO: 2, as calculated by homology search software such as FASTA or BLAST using default parameters.

It should be noted that the identity of amino acid sequences or nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, blastp, tblastn and tblastx have been developed (Altschul SF, et al: J Mol Biol 215: 403, 1990). If blastn is used for nucleotide sequence analysis, parameters may be set to, for example, score=100 and wordlength=12. Likewise, if blastp is used for amino acid sequence analysis, parameters may be set to, for example, score=50 and wordlength=3. If BLAST and Gapped BLAST programs are used, default parameters in each program may be used.

The above polynucleotides according to the present invention can be obtained by known genetic engineering procedures or known synthesis procedures.

2. Proteins of the Present Invention

The present invention provides proteins shown in (i) to (iv) below.

(i) a protein which is encoded by any of the polynucleotides shown in (a) to (e) above;
(ii) a protein which comprises the amino acid sequence shown in SEQ ID NO: 2;
(iii) a protein which comprises an amino acid sequence with deletion, substitution, insertion and/or addition of one or more amino acids in the amino acid sequence shown in SEQ ID NO: 2 and which has an activity to promote fatty acid chain elongation; and
(iv) a protein which has an amino acid sequence sharing an identity of 75% or more with the amino acid sequence shown in SEQ ID NO: 2 and which has an activity to promote fatty acid chain elongation.

The above protein (iii) or (iv) is typically a mutant of the naturally occurring protein shown in SEQ ID NO: 2, although other examples include those which may be artificially obtained by site-directed mutagenesis as described in "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the expression "protein which consists of an amino acid sequence with deletion, substitution, insertion and/or addition of one or more amino acids in the amino acid sequence shown in SEQ ID NO: 2 and which has an activity to promote fatty acid chain elongation" is intended to include proteins which consist of an amino acid sequence with deletion, substitution, insertion and/or addition of, e.g., 1 to 100 amino acid residues, 1 to 90 amino acid residues, 1 to 80 amino acid residues, 1 to 70 amino acid residues, 1 to 60 amino acid residues, 1 to 50 amino acid residues, 1 to 40 amino acid residues, 1 to 39 amino acid residues, 1 to 38 amino acid residues, 1 to 37 amino acid residues, 1 to 36 amino acid residues, 1 to 35 amino acid residues, 1 to 34 amino acid residues, 1 to 33 amino acid residues, 1 to 32 amino acid residues, 1 to 31 amino acid residues, 1 to 30 amino acid residues, 1 to 29 amino acid residues, 1 to 28 amino acid residues, 1 to 27 amino acid residues, 1 to 26 amino acid residues, 1 to 25 amino acid residues, 1 to 24 amino acid residues, 1 to 23 amino acid residues, 1 to 22 amino acid residues, 1 to 21 amino acid residues, 1 to 20 amino acid residues, 1 to 19 amino acid residues, 1 to 18 amino acid residues, 1 to 17 amino acid residues, 1 to 16 amino acid residues, 1 to 15 amino acid residues, 1 to 14 amino acid residues, 1 to 13 amino acid residues, 1 to 12 amino acid residues, 1 to 11 amino acid residues, 1 to 10 amino acid residues, 1 to 9 amino acid residues (one or several amino acid residues), 1 to 8 amino acid residues, 1 to 7 amino acid residues, 1 to 6 amino acid residues, 1 to 5 amino acid residues, 1 to 4 amino acid residues, 1 to 3 amino acid residues, 1 to 2 amino acid residues, or a single amino acid residue in the amino acid sequence shown in SEQ ID NO: 2 and which have an activity to promote fatty acid chain elongation. In general, a smaller number is more preferred for the above deletion, substitution, insertion and/or addition of amino acid residues.

Moreover, examples of such proteins include those which have an amino acid sequence sharing an identity of 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence shown in SEQ ID NO: 2 and which have an activity to promote fatty acid chain elongation. In general, a larger value is more preferred for the above identity.

If a certain protein has an "activity to promote fatty acid chain elongation," when this protein is expressed in appropriate host cells (e.g., yeast, lipid-producing fungi and plant cells), these cells increase their content of fatty acids having more carbon atoms among fatty acids which can be synthesized by these cells, in comparison with cells of the same type where the protein is not expressed. In this case, for synthesis of the above "fatty acids having more carbon atoms," fatty acids having two less carbon atoms are used, and hence the amount of these fatty acids having two less carbon atoms may be reduced.

More specifically, when a protein having an activity to promote fatty acid chain elongation is expressed in the above appropriate host cells, these cells show (i) a decrease in the amount of fatty acids having 16 carbon atoms and an increase in the amount of fatty acids having 18 carbon atoms, (ii) a decrease in the amount of fatty acids having 17 carbon atoms and an increase in the amount of fatty acids having 19 carbon atoms, (iii) a decrease in the amount of fatty acids having 18 carbon atoms and an increase in the amount of fatty acids having 20 carbon atoms, (iv) a decrease in the amount of fatty acids having 20 carbon atoms and an increase in the amount of fatty acids having 22 carbon atoms, (v) a decrease in the amount of fatty acids having 22 carbon atoms and an increase in the amount of fatty acids having 24 carbon atoms, (vi) a decrease in the amount of fatty acids having 24 carbon atoms and an increase in the amount of fatty acids having 26 carbon atoms, (vii) a decrease in the amount of fatty acids having 26 carbon atoms and an increase in the amount of fatty acids having 28 carbon atoms, or (viii) a decrease in the amount of fatty acids having 28 carbon atoms and an increase in the amount of fatty acids having 30 carbon atoms, in comparison with cells of the same type where the protein is not expressed.

It should be noted that the activity to promote fatty acid chain elongation may be measured as described in Han, G. et al., (2002) J. Biol. Chem. 277, 35440-35449.

In addition, for confirmation of the activity to promote fatty acid chain elongation, experiments using appropriate host cells such as yeast, lipid-producing fungi and plant cells may be exemplified. When a polynucleotide encoding the protein of the present invention is expressed in host cells, a protein or peptide encoded by this polynucleotide can be determined as having an activity to promote fatty acid chain elongation if the production of longer chain fatty acids is increased. In the Example section, the inventors of the present invention have confirmed a decrease in the amount of fatty acids having 16 carbon atoms and an increase in the amount of fatty acids having 18 carbon atoms when the protein of the present invention is expressed in yeast cells and the composition of fatty acids contained in these yeast cells is analyzed by gas chromatography.

Since yeast is able to synthesize fatty acids having up to 18 carbon atoms, the amount of fatty acids having 18 carbon atoms was increased in the Example section. If cells capable of synthesizing fatty acids having more than 18 carbon atoms, e.g., fatty acids having 19 or 20 carbon atoms (e.g., *Mortierella alpina*) are used as host cells, there would be an increase in the amount of fatty acids having more carbon atoms (e.g., fatty acids having the most carbon atoms) (e.g., fatty acids having 20 carbon atoms in the case of *Mortierella alpina*) among fatty acids which can be synthesized by the host cells.

The protein of the present invention preferably exerts its activity to promote chain elongation on fatty acids contained in triacylglycerols.

Moreover, fatty acids to be elongated by the protein of the present invention may be either saturated fatty acids or unsaturated fatty acids, preferably unsaturated fatty acids, more preferably monovalent, divalent, trivalent or tetravalent unsaturated fatty acids.

Since the protein of the present invention is a homolog protein of yeast AYR1 protein, it would have β-ketoacyl reductase activity as in the case of AYR1. In yeast, not only AYR1, but also IFA38 is known as a gene having β-ketoacyl reductase activity, and it is also known that simultaneous deletion of both genes is lethal (Han, G. et al., (2002) J. Biol. Chem. 277, 35440-35449). Whether or not the protein of the present invention has β-ketoacyl reductase activity can be confirmed by determining whether or not a yeast strain whose AYR1 and IFA38 genes are disrupted can grow or its β-ketoacyl reductase activity is compensated when the protein of the present invention is expressed therein.

Deletion, substitution, insertion and/or addition of one or more amino acid residues in the amino acid sequence of the protein of the present invention is intended to mean that deletion, substitution, insertion and/or addition of one or more amino acid residues occurs at any one or more positions in the same sequence, and two or more of deletion, substitution, insertion and addition may occur at the same time.

Examples of interchangeable amino acid residues are shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

Moreover, the protein of the present invention may be prepared by chemical synthesis methods such as Fmoc method (fluorenylmethyloxycarbonyl method) and tBoc method (t-butyloxycarbonyl method). Alternatively, the protein of the present invention may also be chemically synthesized with peptide synthesizers commercially available from Advanced Automation Peptide Protein Technologies, Perkin Elmer, Protein Technologies, PerSeptive, Applied Biosystems, SHIMADZU, etc.

3. Vector of the Present Invention and Transformant Transformed with the Same

In another embodiment, the present invention also provides an expression vector containing the polynucleotide of the present invention.

The vector of the present invention is generally configured to comprise:
(i) a promoter transcribable in host cells;
(ii) a polynucleotide shown in any of (a) to (g) above, which is ligated to the promoter; and
(iii) an expression cassette comprising, as constituent elements, signals that function in the host cells for transcription termination and polyadenylation of an RNA molecule.

The thus configured vector is introduced into host cells. Examples of appropriate host cells used in the present invention include lipid-producing fungi, yeast and so on.

As lipid-producing fungi, strains as found in MYCOTAXON, Vol. XLIV, No. 2, pp. 257-265 (1992) can be used. Specific examples include microorganisms belonging to the genus *Mortierella*, as exemplified by microorganisms belonging to the subgenus *Mortierella* such as *Mortierella elongate* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, etc., as well as microorganisms belonging to the subgenus *Micromucor* such as *Mortierella isabellina* CBS194.28, IFO6336, IFO7824, IFO7873, IFO7874, IFO8286, IFO8308, IFO7884, *Mortierella nana* IFO8190, *Mortierella ramanniana* IFO5426, IFO8186, CBS112.08, CBS212.72, IFO7825, IFO8184, IFO8185, IFO8287, *Mortierella vinacea* CBS236.82, etc. Particularly preferred is *Mortierella alpina*.

Likewise, examples of yeast include *Saccharomyces cerevisiae* EH13-15, NBRC1951, NBRC1952, NBRC1953, NBRC1954, etc.

These host cells transformed with the vector of the present invention show an increase in the amount of longer chain fatty acids (e.g., fatty acids having 18, 19 or 20 carbon atoms or fatty acids having more carbon atoms), in comparison with host cells which are not transformed with the vector of the present invention. Preferably, the above fatty acids are those contained in triacylglycerols (which are also referred to as "triglycerides").

For introduction into lipid-producing fungi, a vector available for use may be, but is not limited to, pDura5 (Appl. Microbiol. Biotechnol., 65, 419-425, (2004)).

For introduction into yeast, any vector may be used as long as it has the ability to express an insert in yeast cells. Examples include pYE22m (Biosci. Biotech. Biochem., 59, 1221-1228, 1995).

For regulation of gene expression in host cells, any combination of promoter and terminator may be used as long as they function in the host cells. Examples include histone H4.1 gene promoter, glyceraldehyde-3-phosphate dehydrogenase gene promoter and so on when used in lipid-producing fungi.

Selection markers available for use in transformation include auxotrophic markers (ura5, niaD, trp1), drug resistance markers (hygromycine, zeocin), geneticin resistance gene (G418r), copper resistance gene (CUP1) (Marin et al., Proc. Natl. Acad. Sci. USA, 81, 337 1984), cerulenin resistance gene (fas2m, PDR4) (Junji Inokoshi et al., Biochemistry, vol. 64, p. 660, 1992; Hussain et al., gene, 101, 149, 1991), etc.

For transformation of host cells, commonly used known techniques can be used. For example, in the case of lipid-producing fungi, it is possible to use electroporation (Mackenxie D. A. et al. Appl. Environ. Microbiol., 66, 4655-4661, 2000) and particle delivery method (descried in JP 2005-287403 A entitled "Breeding Method of Lipid Producing Fungi"). Likewise, in the case of yeast, transformation may be accomplished by, but is not limited to, electroporation, spheroplast method (Proc. Natl. Acad. Sci. USA, 75 p 1929 (1978)), lithium acetate method (J. Bacteriology, 153, p 163 (1983)), and other methods as described in Proc. Natl. Acad. Sci. USA, 75 p 1929 (1978), Methods in yeast genetics, 2000 Edition: A Cold Spring Harbor Laboratory Course Manual.

In addition, as for standard cloning techniques, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc.

4. Method for Preparing a Lipid or Fatty Acid Composition According to the Present Invention In yet another embodiment, the present invention also provides a method for preparing a lipid or fatty acid composition by using the above transformed lipid-producing fungus or yeast.

As used herein, the term "lipid" is intended to mean a simple lipid including a compound (e.g., glyceride) which is composed of a fatty acid and an alcohol attached via an ester linkage, or an analog (e.g., cholesterol ester) thereof; a complex lipid which is generated from such a simple lipid by partial modification with phosphoric acid, amino acid(s), saccharide(s) or the like; or a derived lipid which is a hydrolysate of the above lipid and is not soluble in water.

As used herein, the term "fat or oil" refers to an ester (glyceride) composed of glycerol and a fatty acid.

As used herein, the term "fatty acid" refers to an aliphatic monocarboxylic acid (i.e., a carboxylic acid having a single carboxyl group and carbon atoms linked in a chain), represented by the general formula RCOOH (wherein R is an alkyl group). Fatty acids include saturated fatty acids having no double bond in the hydrocarbon chain and unsaturated fatty acids having double bonds in the hydrocarbon chain.

The lipid or fatty acid composition of the present invention can be extracted as follows from cells which have been transformed in accordance with the present invention:

After being cultured, a transformed strain of an organism (e.g., lipid-producing fungus or yeast) is treated in a standard manner, e.g., by centrifugation or filtration to obtain cultured cells. The cells are washed well with water and preferably further dried. Drying may be accomplished by freeze-drying, air-drying, etc. The dried cells are optionally homogenized, e.g., with a Dynomil or by ultrasonication, and then extracted with an organic solvent preferably under a nitrogen stream. Organic solvents used for this purpose include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. When the organic solvent is distilled off from the extract under reduced pressure, fatty acid-containing lipids can be obtained. The extracted fatty acids may be converted into corresponding methyl esters by the hydrochloric acid-methanol method, etc.

Moreover, fatty acids can be separated in a state of mixed fatty acids or mixed fatty acid esters from the above fatty acid-containing lipids by concentration and separation in a standard manner (e.g., urea addition, separation under cooling, column chromatography).

Lipids prepared by the method of the present invention are preferably triacylglycerols, more preferably triacylglycerols containing fatty acids having 18 or more carbon atoms.

Likewise, fatty acids prepared by the method of the present invention are preferably fatty acids having 18 or more carbon atoms, more preferably fatty acids having 18 or more carbon atoms contained in triacylglycerols.

Examples of fatty acids having 18 or more carbon atoms include, but are not limited to, stearic acid (18:0), oleic acid (18:1(9)), vaccenic acid (18:1(11)), linolic acid (18:2(9,12)), α-linolenic acid (18:3(9,12,15)), γ-linolenic acid (18:3(6,9,12)), eleostearic acid (18:3(9,11,13)), arachidic acid (20:0), eicosenoic acid (20:1Δ11), 8,11-eicosadienoic acid (20:2(8,11)), 5,8,11-eicosatrienoic acid (20:3(5,8,11)), arachidonic acid (20:4(5,8,11,14)), behenic acid (22:0), lignoceric acid (24:0), nervonic acid (24:1), cerotic acid (26:0), montanoic acid (28:0) and melissic acid (30:0).

Moreover, fatty acids prepared by the method of the present invention may be either saturated fatty acids or unsaturated fatty acids, preferably unsaturated fatty acids, more preferably monovalent, divalent, trivalent or tetravalent unsaturated fatty acids.

It should be noted that lipids produced by the method of the present invention and fatty acids contained in these lipids can be confirmed for their composition by the above procedures for lipid extraction or fatty acid separation or combinations thereof.

Lipid or fatty acid compositions obtained by the method of the present invention can be provided for use in, e.g., manufacture of fat- or oil-containing foods, pharmaceutical preparations and/or industrial raw materials (e.g., raw materials for cosmetic preparations, soaps, etc.) according to standard practice.

In yet another embodiment, the present invention also provides a method for manufacturing a food, a cosmetic preparation, a pharmaceutical preparation, a soap or the like by using the transformed lipid-producing fungus or transformed yeast of the present invention. This method involves the step of producing lipids or fatty acids by using the transformed lipid-producing fungus or transformed yeast of the present invention. A food, a cosmetic preparation, a pharmaceutical preparation, a soap or the like, each containing the produced lipids or fatty acids, may be prepared in a standard manner. In this way, such a food, a cosmetic preparation, a pharmaceutical preparation, a soap or the like, each being manufactured by the method of the present invention, contains lipids or fatty acids produced by using the transformed lipid-producing fungus or transformed yeast of the present invention. The present invention further provides the thus manufactured food, cosmetic preparation, pharmaceutical preparation, soap or the like.

The cosmetic preparation (composition) or pharmaceutical preparation (composition) of the present invention may be in any dosage form, such as solution, paste, gel, solid, powder and other dosage forms. Moreover, the cosmetic composition or pharmaceutical composition of the present invention may be used in cosmetics or external preparations for skin (e.g., oil, lotion, cream, emulsion, gel, shampoo, hair conditioner, nail enamel, foundation, lipstick, face powder, facial pack, ointment, perfume, powder, eau de cologne, dentifrice, soap, aerosol, cleansing foam), as well as protective and/or ameliorative agents for skin aging, protective and/or ameliorative agents for skin inflammation, bath preparations, hair growth promoters, skin essences, sunscreening agents, or protective and/or ameliorative agents for skin troubles caused by wounds, chaps or cracks on the skin, etc.

When required, the cosmetic composition of the present invention may further be blended as appropriate with additional ingredients such as fats or oils, and/or dyes, aromatics, antiseptics, surfactants, pigments, antioxidants, etc. The blending ratio of these ingredients may be determined by those skilled in the art as appropriate for the intended purpose (e.g., fats or oils may be contained in the composition at a ratio of 1% to 99.99% by weight, preferably 5% to 99.99% by weight, more preferably 10% to 99.95% by weight). Likewise, the pharmaceutical composition of the present invention may further comprise additional pharmaceutically active ingredients (e.g., anti-inflammatory ingredient) or auxiliary ingredients (e.g., lubricating ingredient, carrier ingredient), when required. For example, additional ingredients commonly used in cosmetics or external preparations for skin include drugs for acne, protective agents for dandruff and itching, antiperspirant deodorants, drugs for burn wounds, anti-mite and anti-louse agents, keratin softeners, drugs for xeroderma, antiviral agents, percutaneous absorption promoters, and so on.

Examples of the food of the present invention include nutritional supplementary foods, health foods, functional foods, children's foods, infant modified milk, premature infant modified milk, geriatric foods and so on. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods, diet foods, etc. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods. The term "infant modified milk" refers to modified milk given to children up to about one year old. The term "premature infant modified milk" refers to modified milk given to premature infants until about 6 months after birth.

These foods and food products may be in the form of natural foods (treated with fats or oils) such as meat, fish and nuts; foods supplemented with fats or oils during preparation (e.g., Chinese foods, Chinese noodles, soups); foods prepared using fats or oils as heating media (e.g., tempura (deep-fried fish and vegetables), deep-fried foods, fried bean curd, Chinese fried rice, doughnuts, Japanese fried dough cookies (karinto)); fat- or oil-based foods or processed foods supplemented with fats or oils during processing (e.g., butter, margarine, mayonnaise, dressing, chocolate, instant noodles, caramel, biscuits, cookies, cake, ice cream); and foods sprayed or coated with fats or oils upon finishing (e.g., rice crackers, hard biscuits, sweet bean paste bread). However, they are not limited to foods containing fats or oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine (sake), medicinal liquor, sweet cooking sherry (mirin), vinegar, soy sauce and miso (bean paste); livestock food products such as yogurt, ham, bacon and sausage; seafood products such as fish cake (kamaboko), deep-fried fish cake (ageten) and puffy fish cake (hanpen); as well as fruit drinks, soft drinks, sports drinks, alcoholic beverages, tea and so on.

The food of the present invention may also be in the form of pharmaceutical formulations such as capsules, or in the form of processed foods such as ordinary fluid diets, semi-digested nourishing diets, elemental diets, drinkable preparations or enteral nutrient preparations, which comprise the fats or lipids of the present invention in admixture with proteins, sugars, fats, trace elements, vitamins, emulsifiers, flavorings, etc.

As described above, when expressed in host cells, the gene of the present invention responsible for the activity to promote fatty acid chain elongation allows efficient production of lipids, particularly triacylglycerols.

Further, the expression level of this gene can be used as an indicator, e.g., in the study of culture conditions and/or the management of culture to ensure efficient production of lipids, particularly triacylglycerols.

EXAMPLES

The present invention will now be described in more detail by way of the following examples, which are not intended to limit the scope of the present invention Genomic analysis of *Mortierella alpina*

*M. alpina* strain 1S-4 was inoculated into 100 ml of GY2:1 medium (2% glucose, 1% yeast extract, pH 6.0) and cultured at 28° C. for 2 days under shaking conditions. The cells were collected by filtration, and their genomic DNA was prepared using DNeasy (QIAGEN). The nucleotide sequence of the above genomic DNA was determined using a Roche 454 GS FLX Standard, during which nucleotide sequencing was conducted in two runs for a fragment library and in three runs for a mate-paired library. The resulting nucleotide sequences were assembled to give 300 supercontigs.

Synthesis of cDNA and Preparation of cDNA Library

*M. alpina* strain 1S-4 was inoculated into 100 ml of medium (1.8% glucose, 1% yeast extract, pH 6.0) and pre-cultured for 3 days at 28° C. A 10 L culture vessel (Able Co., Tokyo) was charged with 5 L of medium (1.8% glucose, 1% soybean powder, 0A% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using an Oligotex-dT30 <Super> mRNA Purification Kit (Takara Bio Inc.), poly(A)$^+$RNA was purified from the total RNA. A cDNA library was prepared for each stage with a ZAP-cDNA GigapackIII Gold Cloning Kit (STRATAGENE).

Search for Homologs of Yeast AYR1

Homologs of ScAYR1 (YIL124W), which is a gene responsible for 1-acyl dihydroxyacetone phosphate reductase activity and β-ketoacyl reductase activity in yeast, were searched against genomic databases. As a result, a hit was found in a supercontig containing the sequence shown in SEQ ID NO: 4. The gene of SEQ ID NO: 4 was designated as MaADR1.

Cloning of MaADR1 cDNA

For cloning of cDNA for the MaADR1 gene, it was predicted that ATG located at positions 1-3 of SEQ ID NO: 4 would be an initiation codon, while positions 1587-1589 of SEQ ID NO: 4 would constitute a termination codon, as judged from the presence of initiation and termination codons as well as sequence comparison with the homolog. Then, the following primers were synthesized.

```
                                          (SEQ ID NO: 5)
Bam-ADR-F: 5'-GGATCCATGGCCTCGTCTAAAAAGATCGTCCT-3'

(SEQ ID NO: 6)
Sal-ADR-R: 5'-GTCGACTACTTTCCAACGACCTTGCCATCC-3'
```

Using the cDNA of *M. alpina* strain 1S-4 as a template, PCR amplification was conducted by KOD-Plus (TOYOBO) with the primers Bam-ADR-F and Sal-ADR-R, whereby a DNA fragment of approximately 0.87 kb was amplified. This fragment was cloned using a Zero Blunt TOPO PCR cloning kit (Invitrogen) and the resulting plasmid was designated as pCR-MaADR1. The sequence of the insert in this plasmid, i.e., the CDS sequence of the MaADR1 gene is shown in SEQ ID NO: 3. In addition, the ORF sequence of the MaADR1 gene is shown in SEQ ID NO: 1.

Sequence Analysis

When a comparison was made between genomic sequence (SEQ ID NO: 4) and CDS sequence (SEQ ID NO: 3) of the MaADR1 gene, the genomic sequence of this gene was found to be composed of five exons and four introns (FIG. 1) and was predicted to encode a protein consisting of 242 amino acid residues (FIG. 2).

The deduced amino acid sequence (SEQ ID NO: 2) of MaADR1 was subjected to BLASTp homology analysis against the amino acid sequences registered in GENEBANK nr. As a result, an amino acid sequence showing the lowest E-value against this sequence, i.e., sharing the highest identity with this sequence was a putative protein derived from *Volvox carterif. nagariensis* (green algae) (GENEBANK accession No. XP_002946364), which shared an amino acid sequence identity of 34.7%. In addition, the deduced amino acid sequence of MaADR1 shared an identity of 25.6% with the amino acid sequence of AYR1p derived from yeast *S. cerevisiae* and 13.6% with the amino acid sequence of IFA38.

FIG. 3 shows an amino acid sequence comparison of MaADR1, the putative protein derived from *Volvox carterif. nagariensis* (green algae) (GENEBANK accession No. XP_002946364) and AYR1p derived from *S. cerevisiae*.

Functional Analysis of MaADR1

Construction of Yeast Expression Vector

A yeast expression vector, pYE22m (Biosci. Biotech. Biochem., 59, 1221-1228, 1995), was digested with restriction enzymes BamHI and SalI to obtain a DNA fragment, while the plasmid pCR-MaADR1 was also digested with restriction enzymes BamHI and SalI to obtain a DNA fragment of approximately 0.87 kbp. These DNA fragments were ligated together using ligation high (TOYOBO) to construct plasmid pYE-MaADR1.

Obtaining of Transformed Yeast

The plasmids pYE22m and pYE-MaADR1 were each used to transform yeast *S. cerevisiae* strain EH13-15 (trp1, MATα) (Appl. Microbiol. Biotechnol., 30, 515-520, 1989) by the lithium acetate method. The transformed strains were screened by the ability to grow on SC-Trp agar medium (2% agar) containing, per liter, 6.7 g of Yeast nitrogen base w/o amino acids (DIFCO), 20 g of glucose and 1.3 g of amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Yeast Culture

Any four strains obtained by transformation with the plasmid pYE22m and any four strains obtained by transformation with the plasmid pYE-MaADR1 were subjected to the following culture experiment. Namely, in the pre-culture step, a loopful of each yeast strain was inoculated from the plate into SC-Trp medium (10 ml) and cultured at 30° C. for 1 day under shaking conditions. In the main culture step, the pre-cultured solution (100 μl) was added to SC-Trp medium (10 ml) and cultured at 30° C. for 2 days under shaking conditions.

Fatty Acid Analysis of Yeast Cells

The cultured yeast solutions were each centrifuged to collect the cells. After washing with 10 ml of sterilized water, the cells were collected again by centrifugation and then lyophilized. To the lyophilized cells, 1 ml of chloroform:methanol (2:1) and glass beads were added and the cells were homogenized with a bead beater, followed by centrifugation to collect the supernatant. To the remaining cells, 1 ml of chloroform:methanol (2:1) was added again and the supernatant was collected in the same manner. This procedure was repeated to collect lipids with chloroform:methanol (2:1) in a total volume of 4 ml. The solvent was distilled off with a SpeedVac. The samples were each dissolved in 1 ml of chloroform.

A 200 μl aliquot of each sample was taken and treated by the hydrochloric acid-methanol method to derive fatty acids into corresponding methyl esters, followed by gas chromatography for fatty acid analysis to determine the composition of total fatty acids in the cells.

The results obtained are shown in Table 1. The strain highly expressing the MaADR1 gene showed an increased proportion of C18 fatty acids and a decreased proportion of C16 fatty acids in total fatty acids, when compared to the control strain. Namely, the chain elongation reaction of fatty acids was activated.

TABLE 1

Relative proportions of total fatty acids in yeast cells

|  | Control | pYE-MaADR1 |
|---|---|---|
| 16:0 | 7.76 ± 0.13 | 7.52 ± 0.24 |
| 16:1 | 34.40 ± 0.76 | 33.70 ± 1.04 |
| 18:0 | 5.78 ± 0.12 | 5.88 ± 0.12 |
| 18:1 | 47.96 ± 0.79 | 49.51 ± 1.26 |
| other | 4.10 ± 0.29 | 3.39 ± 0.12 |

Mean ± SD

A 400 μl aliquot was taken from each of the above samples. After distilling off the solvent, the residue was dissolved in a small volume of chloroform and provided for thin-layer chromatography. Namely, under conditions using a silica gel 60 plate (Merck & Co., Inc.) and a developing solvent, hexane: diethyl ether:acetic acid (70:30:1), thin-layer chromatography was performed to fractionate lipids. The plate was sprayed with a primulin solution and irradiated with ultraviolet light to detect the lipids. The triacylglycerol (TG) fraction and the phospholipid (PL) fraction were scraped into separate test tubes and treated by the hydrochloric acid-methanol method to derive fatty acids into corresponding methyl esters, followed by gas chromatography for fatty acid analysis.

Tables 2 and 3 show the composition of fatty acids in the triacylglycerol fraction and the composition of fatty acids in the phospholipid fraction, respectively.

TABLE 2

Relative proportions of fatty acids in the triacylglycerol fraction in yeast cells

|  | Control | pYE-MaADR1 |
|---|---|---|
| 16:0 | 7.25 ± 0.17 | 6.81 ± 0.20 |
| 16:1 | 35.70 ± 0.21 | 34.34 ± 0.39 |
| 18:0 | 6.96 ± 0.13 | 7.06 ± 0.11 |
| 18:1 | 43.90 ± 0.21 | 46.26 ± 0.47 |
| other | 6.19 ± 0.24 | 5.54 ± 0.08 |

Mean ± SD

TABLE 3

Relative proportions of fatty acids in the phospholipid fraction in yeast cells PL

|  | Control | pYE-MaADR1 |
|---|---|---|
| 16:0 | 10.99 ± 0.09 | 10.97 ± 0.24 |
| 16:1 | 38.15 ± 0.83 | 38.48 ± 1.48 |
| 18:0 | 5.53 ± 0.23 | 5.75 ± 0.21 |
| 18:1 | 42.02 ± 0.81 | 42.48 ± 0.99 |
| other | 3.31 ± 0.09 | 2.32 ± 1.55 |

Mean ± SD

Focusing on the composition of fatty acids in the triacylglycerol fraction, the strain highly expressing MaADR1 showed an increased proportion of C18 fatty acids and a decreased proportion of C16 fatty acids, when compared to the control. On the other hand, focusing on the composition of fatty acids in the phospholipid fraction, the strain highly expressing MaADR1 and the control strain showed almost the same proportions of fatty acids.

Namely, when MaADR1 was highly expressed in yeast cells, the composition of fatty acids constituting triacylglycerols was changed in such a way as to increase the proportion of longer chain fatty acids.

Industrial Applicability

When expressed in appropriate host cells, the polynucleotide of the present invention allows efficient production of long chain fatty acids having 18 or more carbon atoms and triacylglycerols containing the same. Fatty acids produced in host cells by the present invention can be used for manufacture of foods, cosmetic preparations, pharmaceutical preparations, soaps, etc.

Sequence Listing Free Text
  SEQ ID NO: 5: synthetic DNA
  SEQ ID NO: 6: synthetic DNA

The invention claimed is:

1. A cDNA comprising a nucleotide sequence of any one selected from the group consisting of (a) to (c) shown below:
   (a) the nucleotide sequence shown in SEQ ID NO: 1 or 4;
   (b) a nucleotide sequence encoding a protein which consists of the amino acid sequence shown in SEQ ID NO: 2; and
   (c) a nucleotide sequence encoding a protein which has an amino acid sequence sharing an identity of 90% or more with the amino acid sequence shown in SEQ ID NO: 2 and which has an activity to promote fatty acid chain elongation.

2. The cDNA according to claim 1, comprising a nucleotide sequence encoding
   a protein which has an amino acid sequence sharing an identity of 95% or more with the amino acid sequence shown in SEQ ID NO: 2 and which has an activity to promote fatty acid chain elongation.

3. The cDNA according to claim 1, which contains the nucleotide sequence shown in SEQ ID NO:1 or 4.

4. The cDNA according to claim 1, which encodes a protein consisting of the amino acid sequence shown in SEQ ID NO: 2.

5. A vector containing the cDNA according to claim 1.

6. A non-human transformant transformed with the cDNA according to claim 1.

7. A non-human transformant transformed with the vector according to claim 5.

8. The transformant according to claim 6, wherein the transformant is a lipid-producing fungus.

9. The transformant according to claim 8, wherein the lipid-producing fungus is *Mortierella alpine*.

10. A method for preparing a lipid or fatty acid composition, which comprises collecting a lipid or fatty acid composition from a cultured product of the transformant according to claim 6.

11. The method according to claim 10, wherein the lipid is a triacylglycerol.

12. The method according to claim 10, wherein the fatty acid has 18 or more carbon atoms.

* * * * *